(12) United States Patent
Lang et al.

(10) Patent No.: US 7,488,573 B2
(45) Date of Patent: Feb. 10, 2009

(54) IN VIVO ANGIOGENESIS ASSAY

(75) Inventors: Richard Anthony Lang, Loveland, OH (US); Ivan Borisovich Lobov, New York, NY (US)

(73) Assignee: Children's Hospital Medical Center, Cincinnati, OH (US)

( * ) Notice: Subject to any disclaimer, the term of this patent is extended or adjusted under 35 U.S.C. 154(b) by 267 days.

(21) Appl. No.: 10/519,527

(22) PCT Filed: Jun. 26, 2003

(86) PCT No.: PCT/US03/20208

§ 371 (c)(1), (2), (4) Date: Jan. 26, 2006

(87) PCT Pub. No.: WO2004/002413

PCT Pub. Date: Jan. 8, 2004

(65) Prior Publication Data

US 2006/0165595 A1 Jul. 27, 2006

Related U.S. Application Data

(60) Provisional application No. 60/391,641, filed on Jun. 26, 2002.

(51) Int. Cl.
*C12Q 1/00* (2006.01)
*C12Q 1/68* (2006.01)
*C12N 5/00* (2006.01)

(52) U.S. Cl. ................. 435/4; 435/6; 435/325; 435/352

(58) Field of Classification Search ............. 424/4, 424/6, 325, 352
See application file for complete search history.

(56) References Cited

U.S. PATENT DOCUMENTS

| | | | |
|---|---|---|---|
| 5,830,879 A | 11/1998 | Isner | |
| 5,935,076 A | 8/1999 | Smith et al. | |
| 5,972,639 A | 10/1999 | Parandoosh | |
| 5,976,782 A | 11/1999 | Parish et al. | |
| 6,133,231 A | 10/2000 | Ferrara et al. | |
| 6,302,850 B1 | 10/2001 | Tsukada et al. | |
| 6,305,804 B1 | 10/2001 | Rice et al. | |
| 6,329,348 B1 | 12/2001 | Crystal et al. | |

FOREIGN PATENT DOCUMENTS

WO     WO 00/47107     8/2000

OTHER PUBLICATIONS

Brown, K.J. et al., A Novel In Vitro Assay for Human Angiogenesis, Lab Invest, Oct. 1996, 75(4), 539-55.

Meeson, Annette, et al., A Relationship Between Apoptosis and Flow During Programmed Capillary Regression is Revealed by Vital Analysis, Development 122, (1996), pp. 3929-3938, 1996, Great Britain.

Lobov, I.B., et al., Angiopoietin-2 Displays VEGF-Dependent Modulation of Capillary Structure and Endothelial Cell Survival In Vivo, PNAS, Aug. 20, 2002, vol. 99, No. 17, pp. 11205-11210.

Lang, R. et al., Apoptosis During Macrophage-Dependent Ocular Tissue Remodelling, Development 120, (1994), pp. 3395-3403 (1994), Great Britain.

Lang, R.A., Apoptosis In Mammalian Eye Development: Lens Morphogenesis, Vascular Regression and Immune Privilege, Cell Death and Differentiation (1997) 4, pp. 12-20.

Aliprantis, A.O. et al., Do Macrophages Kill Through Apoptosis? Immunology Today, Dec. 1996, vol. 17, No. 12, pp. 573-576.

Lang, R.A., et al., Macrophages and Required for Cell Death and Tissue Remodeling in the Developing Mouse Eye, Cell Aug. 13, 1993, vol. 74, pp. 453-462.

Diez-Roux, Graciana et al., Macrophages Induce Apoptosis in Normal Cells In Vivo, Development 124, (1997), pp. 3633-3638, (1997), Great Britain.

Diez-Roux, Graciana et al., Macrophages Kill Capillary Cells in $G_1$ Phase of the Cell During Programmed Vascular Regression, Development 126, (1999), pp. 2141-2147, (1999), Great Britain.

Meeson, Annette P., et al., VEGF Deprivation-Induced Apoptosis is a Component of Programmed Capillary Regression, Development 126, (1999), pp. 1407-1415, (1999), Great Britain.

Yanagawa, Toshihiro, et al, Aqueous Vascular Endothelial Growth Factor and Basic Fibroblast Growth Factor Decrease During Regression of Rabbit Pupillary Membrane, Japanese Journal of Opthalmology, vol. 42, Issue 3, May 6, 1998, pp. 157-161.

Ito, M, et al., Regression of the Hyaloid Vessels and Pupillary Membrane of the Mouse, Anat Embryol (Berl), Oct. 1999; 200(4): 403-11.

*Primary Examiner*—Ruth A Davis
(74) *Attorney, Agent, or Firm*—Daniel F. Nesbitt; Hasse & Nesbitt LLC

(57) ABSTRACT

A method for evaluating in vivo a test substance for angiogenesis modulation activity, including the steps of providing a rodent pup having a pupillary membrane system in a first eye, injecting transcorneally proximate to the pupillary membrane a test substance; and examining the pupillary membrane to determine whether new vascular tissue has grown. The method can also evaluate the ability of a test substance to regress existing vascular tissue, or to inhibit or prevent new vascular tissue, by injecting transcorneally a first substance that induces new vascular tissue growth, then injecting a test substance, and examining the pupillary membrane to determine whether new vascular tissue has grown. The assay can also be used to evaluate the effect of a small molecule on a property of a capillary vessel, and to evaluate a test substance on a problematic vascular condition.

18 Claims, 1 Drawing Sheet

IN VIVO ANGIOGENESIS ASSAY

CROSS REEERENCE TO RELATED APPLICATIONS

This is the National Stage of International Application PCT/US2003/20208, with an international filing date of Jun. 26, 2003, which claimed the benefit of Provisional Application No. 60/391,641, filed on Jun. 26,2002.

FIELD OF THE INVENTION

The present invention relates to an assay for screening substances to identify modulators of angiogenesis. In particular, the invention provides a method for in vivo screening of substances that modulate angiogenesis.

BACKGROUND OF THE INVENTION

Angiogenesis, or the development of new blood vessels from pre-existing blood vessels, is an essential feature of tissue development and wound healing. Without the appropriate development of a blood supply, tissues cannot survive. The circulatory system is essential for the supply of oxygen and nutrients to tissues and for the removal of by-products of metabolism.

Angiogenesis is normally observed in wound healing, fetal and embryonal development, and formation of the corpus luteum, endometrium and placenta. The control of angiogenesis is a highly regulated system of angiogenic stimulators and inhibitors. Thus, angiogenesis is a critical component of the body's normal physiology. In adults, angiogenesis is a relatively rare occurrence except during wound healing and in the ovaries during the sexual cycle.

However, there are a number of "angiogenesis-dependent diseases" in adults where angiogenesis is important. The most important of these is the angiogenesis associated with the growth of solid tumors, hemaniomas, proliferative retinopathies and rheumatoid arthritis. Certain disease states can alter the control of angiogenesis and, in many cases, the pathological damage associated with the disease is related to uncontrolled angiogenesis. Uncontrolled angiogenesis can act detrimentally when blood vessels multiply and enhance the growth and metastasis of tumors. Aberrant angiogenesis is also associated with numerous disorders, including rheumatoid arthritis, where blood vessels invade the joint and destroy cartilage, and numerous ophthalmologic pathologies, such as diabetic retinopathies in which new capillaries invade the vitreous, bleed and cause blindness. Angiogenesis can also play a significant part in other diseases, such as coronary artery disease and restenosis following angioplasty.

Angiogenesis is essential to tumor development and growth. An angiogenesis inhibitor may therefore stop or inhibit the growth of primary tumors, impede or reduce the formation of metastases, and impede the appearance of secondary growths. Angiogenic inhibitors are also useful in the treatment of non-neoplastic disorders in which an angiogenic activity occurs.

The development of angiogenesis inhibitors can provide a means for controlling these diseases. Compounds that have anti-angiogenic activity can be used, for example, as anti-tumor agents and for the treatment of ophthalmic disorders, particularly involving the retina and vitreous humor, and for hyperproliferative dermatological disorders, such as psoriasis, that have an angiogenic component. Thus, there is an important need to identify compounds that enhance angiogenesis, and compounds that inhibit angiogenesis.

Assays and methods to study angiogenesis can be conducted either in vivo or in vitro. An in vitro method can include the method described in U.S. Pat. No. 5,976,782, issued to Parish at al. on Nov. 2, 1999, related to determining angiogenesis by culturing a blood vessel fragment in a physiological gel, and testing substances on the gel to determine their angiogenic effects. Other in vitro assays have usually entailed establishing long term cultures of endothelial cells and inducing formation of microvessels by placing the cells on extracellular matrices or exposing the cells to various angiogenic stimuli. Such assays are highly artificial and may not represent a physiological response, particularly as the endothelial cells are already activated, having been cultured for considerable periods of time in the presence of growth factors before use.

There remain significant drawbacks to in vitro assays and methods. An in vitro sample of a tissue is disconnected from the remainder of the body system, prohibiting stimulation to, or stimulation from, other body tissues, compounds, and functions. The in vitro method provides no signal of the cellular stimuli caused by the test compound to the body, and no feedback from the body to the affected cells. Therefore, while there are unique advantages to the use of an in vitro assay, in vivo studies remain as an important assay in the development of medical drugs and products.

Three commonly-used in vivo assays for angiogenesis are the rabbit corneal pocket, the hamster cheek pouch, and the chicken chorioallantoic membrane (CAM) assays. In each system an angiogenic substance is implanted in the cornea, cheek pouch, or the CAM, respectively, in order to induce angiogenesis. The corneal pocket and cheek pouch in vivo assays do not provide a clear view of the capillary system, including the endothelial cell walls. The CAM chick assay involves a species (the chicken) that is too distant to be useful for assessing angiogenic modulating agents and their effects in mammals including humans.

The pupillary membrane (PM) is a unique in vivo model system that has been discovered to have unique advantages as an in vivo assay for angiogenic modulators. This structure is a temporary vascular network that surrounds the anterior part of the lens in the developing eye. In humans, the PM is present only during embryogenesis as it regresses during the third trimester, although there are rare cases of a pupillary membrane persisting after birth (persistent pupillary membrane). In many species of the rodent family, regression occurs in the second week after birth. Being situated in the anterior chamber of the eye, the PM can be visualized vitally and is accessible for manipulation in vivo via trans-corneal injection. Since the PM is composed of a two-dimensional array of microcapillaries that can be rapidly dissected from the eye, this structure is uniquely suited to test the immediate in vivo response of microvessels to angiogenic modulators.

Therefore it is an object herein to provide an improved in vivo method for identifying compounds that modulate vascular and endothelial cell proliferation and inhibition. In particular, it is an object herein to provide an in vivo method for screening for both pro- and anti-modulators of angiogenesis. It is also an object to define a method for evaluating in vivo the angiogenic effect of small molecules and chemical substances.

SUMMARY OF THE INVENTION

The present invention relates to a method for evaluating in vivo the angiogenic activity of a test substance, such as an angiogenic modulator. The method can be used to evaluate in vivo whether an angiogenic enhancing substance can effect the growth of new vascular tissue. The method uses the pupillary membrane of a rodent pup, and comprises the steps of a) providing a rodent pup having a pupillary membrane system in a first eye, b) injecting transcorneally proximate to the pupillary membrane a test substance; and c) examining the pupillary membrane to determine whether new vascular tissue has grown.

The invention also relates to a method for evaluating in vivo whether an angiogenic regressor substance can inhibit or prevent the growth of new vascular tissue. The method can comprise the steps of a) providing a rodent pup having a pupillary membrane system in a first eye, b) injecting transcorneally proximate to the pupillary membrane a first composition comprising a first substance that can induce new vascular tissue growth; c) injecting transcorneally proximate to the pupillary membrane a second composition comprising a test substance; and d) examining the pupillary membrane to determine whether new vascular tissue has grown.

The invention also relates a method to evaluate in vivo the effect on a property of a capillary vessel structure by a small molecule test substance. The method can comprise the steps of a) providing a rodent pup having a pupillary membrane system in a first eye, b) injecting transcorneally proximate to the pupillary membrane a first composition comprising a small molecule test substance; and c) examining the pupillary membrane to determine the effect of the test substance on the property of the capillary vessel structure of the pupillary membrane.

DETAILED DESCRIPTION OF THE INVENTION

Definitions

Figure 1:
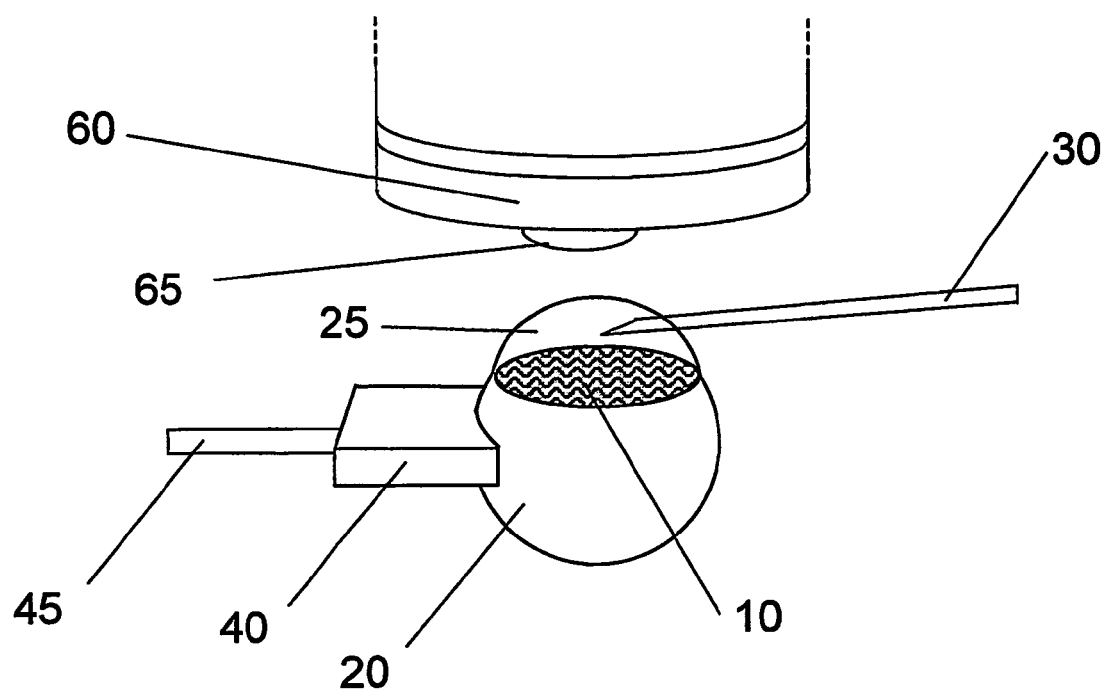
FIG. 1 shows devices for holding and illuminating, for observing, and for injecting a test substance onto, the pupillary membrane of an eye.

The term "pupillary membrane (or PM)" means the transient vascular network traversing the pupillary opening of the iris in the eye of mammals.

The term "angiogenesis modulation" refers to the ability of a substance to modulate or change normal angiogenic activity of the blood vessel fragments and includes inhibition and enhancement of angiogenic activity. The method can be used to test substances that are possible angiogenesis enhancers (pro-angiogenic substance) or possible angiogenesis regressors (anti-angiogenic substance).

The term "rodent pup" refers to a postnatal member of the rodent family, and is typically a rat or mouse.

The term "anti-angiogenic agent" means any substance that inhibits angiogenesis, and can also be referred to as an angiogenic inhibitor or angiogenic regressor substance.

The Method and Assay

The PM permits study of the capillary system in an in vivo environment. The availability of the PM provides a unique view of the angiogenesis process in the capillary systems at the cellular level.

The examination of the subject's pupillary membrane for angiogenic activity includes examination for new capillary vessel structure, diminished capillary vessel structure, strengthening of the capillary vessel structure, and combinations thereof. The examination is preferably done with the aid of an optical or digital microscope, having sufficient resolution to view activity at the cellular and sub-cellular levels. The examination can use a computer analysis of at least one image of the pupillary membrane system.

Angiogenesis can be identified by the rapid increase in the diameter of existing capillaries, observable through a light microscope. Angiogenesis can also be identified by the remodeling of the basal lamina of capillary vessels as new vessels sprout from existing ones. The remodeling of basal lamina is accompanied by the denaturing or cleavage of collagen in the basal lamina of the vascular vessels, which can be detected by using a monoclonal antibody, such as MAb HU177. (See Xu et al., *Hybridoma,* 19:375-385 (2000), incorporated herein by reference). HU177 antibody recognizes different collagen types including the interstitial matrix collagen type I and the blood vessel basal lamina collagen type IV. The present of staining indicates collagen (basal lamina) remodeling has taken place.

Angiogenesis can also be manifested by migration of endothelial cells from capillary vessels. The presence of cell migration is indicated by the presence of VE-cadherin positive cells outside the confines of existing capillaries, VE-cadherin being a marker for vascular endothelial cells.

Providing a Rodent Pup

The first step of the method comprises providing a rodent pup having a vital pupillary membrane system in a first eye. The rodent pup, as well as its pupillary membrane(s), should be vital: alive and healthy. Any postnatal rodent can provide a suitable subject provided it has its postnatal PM. Preferably, the supply of subjects is maintained from a consistent breed of rodents. Suitable rat and mice pups can be obtained from commercial breeders, such as Sprague-Dawley rats available from Taconic Farms (German Town, N.Y.). The age of newborn rats can be determined by the presence of sperm in a vaginal fluid smear in the breeding female and the time of conception assigned to the previous midnight. Ages of rats are noted as days postconception (for example, "p.c. 31.5" means 31.5 days after conception).

The rodent pup is prepared by anaesthetizing and restraining the rodent subject. Commercially-available anesthetics can be used to subdue and anaesthetize the pup. Metaphane makes a suitable means of subduing the pup. Ketamine and/or xylazine can be injected intramuscularly or subcutaneously to anaesthetize the pup prior to preparation of the subject's eyes for injection. A local anesthetic, such as tetracaine hydrochloride, can be used on the cornea to eliminate sensation prior to parting the eyelid and injecting the test substance. Once anaesthetized, the rat pup's eyelids are folded out of the way to provide a clear view of the PM through the cornea. The anesthetized pup is restrained to restrict any movement, and kept warm to avoid both discomfort and any involuntary body response. A preferred means to restrain the pup comprises a silastic body mold formed to fit the body shape of a rodent pup. The silastic body mold holds the rodent pup in a position that provides easy access to either of the pup's eyes. Preferably, the mold holds the pup on either its left or right side so that the opposed eye is accessible to injection and/or observation.

FIG. 1 shows an eye 20 of a rodent pup (not shown), having a cornea 25 and a pupillary membrane 10. An eye holder 40 is placed against the eye to press gently the eye against the eye socket, thereby limiting movement (e.g., rotation) of the eye. The eye holder can be made from a plastic material, such as nylon, that is easily molded or shaped, and which is preferably translucent to permit the transmission of light therethrough. The eye holders 40 preferably supports a light source 45 for illuminating the eye interior. A preferred light source 45 is a 1-mm diameter optic fiber positioned within the translucent eye holder. The interior of the eye including the pupillary membrane 10 can be viewed with a microscope 60 through its objective 65. A test substance can be injected proximate the pupillary membrane 10, and preferably directly onto the pupillary membrane 10, using an injection means such as a beveled glass needle 30 that can penetrate the cornea 25 to deliver the test substance above the pupillary membrane. Preferably the beveled glass needle 30 is supported with a micromanipulator (not shown) to improve control of the needle as it is inserted through the cornea, and to hold the needle in place. Preferably, the injection means is inserted into the eye on a side opposed to the illuminated eye holder 40.

Injecting the Test Substance

Once anaesthetized and restrained, one or more compositions comprising the test substance and any standard substance can be injected through the corneal tissue and onto the PM. A preferred means of injection is a bevel glass needle. A defined volume of a test substance can be delivered to the anterior chamber of the eye, such as with a Nanoject II Variable Volume Injector (for example, model 3-000-204), available from Drummond Scientific Company, PA).

The quantity of test composition to be injected will vary depending upon the strength and concentration of the test substance. Typically, the amounts will vary from about 0.001-1.00 microliters of test composition. Based on the volume of the anterior chamber of a rodent pup of about 10 microliters, the amount of test composition is generally about 0.1-100 micrograms substance/milliliter anterior chamber volume.

During and after the injection, the progress of angiogenesis of the PM can be tracked vitally for up to several hours, typically up to about 4 hours. The limited time to track the vital PM is imposed by a number of factors including reduced image quality due to gradual opacification of the cornea and sensitivity of the subject to repeated doses of anesthesia The injection procedure can be viewed with a stationary microscope, typically with a 5× air objective. An aqueous immersion objective (10× to 40×) is preferably used to view an immediate response vitally at the pupillary membrane within the eye.

Examining the PM

After a prescribed time for angiogenic progress, the rodent pup is humanely sacrificed, and the pupillary membrane is harvested. The harvesting comprises separating the pupillary membrane and any support structure from the remainder of the eye. Preferably the pupillary membrane is removed with the lens-iris diaphragm complex. The dissection begins with removal of the eyeball (or "orbit"), its immersion in phosphate-buffered saline (PBS) and piercing of the sclera and choroid with the tip of a dissection knife (Storz, St. Louis, Mo.) in the vicinity of the optic nerve. A longitudinal incision is then made with 7 mm blade curved tip vannas (Storz, St. Louis, Mo.) forward as far as the cornea and then continued perpendicularly along the cornealscleral junction. Vessels of the hyaloid system including the hyaloid artery are then severed to allow separation and disposal of the sclera, choroid and retina from the lens, cornea and iris diaphragm. The latter tissue group is then oriented cornea down, the lens capsule pierced and the lens partially collapsed. The lens is then peeled gently away from the iris diaphragm and cornea to expose the PM. At this stage, the tissue was fixed for 30 minutes in PBS containing 4% formaldehyde. The tissue was then reimmersed in PBS alone and the dissection completed. This required making tangential incisions around the periphery of the iris diaphragm and cornea so that the two structures could be separated. The PM and iris diaphragm were then laid flat on a slide ready for examination with an optical or a scanning electron microscope, using commonly used preparation techniques.

Dissection of the PM is needed to provide optimum viewing and study of the angiogenic effects of the test substance. For example, staining of cells and tissue of the PM can provide better detail of the structure of the vascular network and the endothelial cells. One staining technique identifies endothelial cell nuclei using 5-bromo-2'-deoxyuridine (or "BrdU"), a nucleoside that can substitute for thymidine in the DNA of a chromosome. The subject is injected intraperitoneally (i.p.) with BrdU (20 mg/ml in 0.007 M NaOH, available from Sigma Chemical Co.) at a dose of 100 mg/g body mass. Loss of BrdU signal due to competing thymidine incorporation can be blocked with 5-fluoro-2'-deoxyuridine (1.4 mg/ml in 0.007 M NaOH, available from Sigma Chemical Co.) at a dose of 6.7 mg/g body mass. The uptake amount of BrdU by a cell is a random process depending upon time, concentration of BrdU, and the number of thymidine in the DNA. However, once taken in and blocked, the amount of BrdU remains constant. Cell division results in a daughter cell and nucleus with the same amount of BrdU as the mother cell. Endothelial cells that incorporate BrdU are detected using a monoclonal rat anti-BrdU antibody (clone BUI/75-1CR1, available from Accurate Chemical and Scientific Corporation, Westbury, N.Y.) at a dilution of 1:50, followed either by a goat anti-rat antibody conjugated to Alexa 488 (Molecular Probes Eugene, Oreg.) or a horseradish peroxidase-conjugated goat anti-rat antibody (Boehringer Mannheim). Both secondary antibodies were used at a dilution of 1:100. (See, Harlow and Lane, 1988, and Diez-Roux et al., *Development*, 126:2141-2147 (1999), each incorporated herein by reference).

The quantity of vascular cells of the PM labeled with BrdU can be estimated using the 40× objective of a Zeiss Axiophot epifluorescence microscope. With the photographic frame of the microscope camera serving to delimit the area of each field, five randomly selected fields are analyzed per PM and used to determine the average percentage of vascular cells incorporating BrdU. Capillary cells that have divided after BrdU incorporation appear as pairs of nuclei with matching labeling intensity. Since some adjacent cells will take up substantially equivalent amounts of BrdU purely by chance, it is important to match labeling intensity of adjacent nuclei as closely as possible to distinguish adjacent, equivalent "single" cells from a divided "pair" of cells.

The images of the progress or results of angiogenesis can be viewed through the microscope, and can be captured and stored as still film or digital images or as a stream of analogue or digital video. A preferred image recording device is a combination of a CCD camera (Sony DXC-760) and a video recorder (Sony Betacam SP UVW-1400. The recorded video can be examined on a frame by frame basis, and used to capture still images. A preferred system uses a Sony Betacam SP PVW-2656 video deck, and a DECpc XL560 computer (Universal Images, New York, N.Y.), operating with Metamorph software and a Matrix frame grabbing board, which can capture and overlap in-focus video frames as a still image. The final still images can be handled using other conventional digital image editing and presentation software, such as Adobe Photoshop and Quark Express.

The responses of the PMs (angiogenic or otherwise) can be quantified manually or by computer based image analysis of photographs, video images or digital images. Preferably the responses are quantified by automated means such as by the NIH IMAGE program. Such quantification provides rapid and accurate assessment of the responses.

The assay of the present invention is particularly well suited to screening inhibitors or enhancers of mammalian, including human angiogenesis.

The methods of the invention can further comprise a step of comparing the new examined tissue growth with that of a control. A control can be the opposed eye of the rodent pup or an eye of another rodent pup, preferably of the same litter. Preferably, the control step comprises examining the pupillary membrane of the other eye into which no test substance has been injected.

The method permits both time-dependent and dose-dependent angiogenic studies of a test substance. Vital access to the PM at the time of injection of the test substance permits assessing an immediate or short term effect on the PM. Time-delayed and multiple-dosage effects can be made by visually reassessing the vital PM, or by harvesting, fixing and examining the PM.

The invention can also be used to evaluate the effect of a test substance on a problematic capillary vessel condition. A problematic capillary vessel condition is generally an unhealthy or abnormal condition that can either be induced or occur naturally in the capillary vessel system. An example of a problematic capillary vessel condition is a blood clot, in which case the test substance can be a blood clot busting candidate substance. The method can comprise the steps of:
 a. providing a rodent pup having a pupillary membrane system in a first eye;
 b. inducing a problematic capillary vessel condition into one or more vessels of the pupillary membrane;
 c. injecting transcorneally proximate to the pupillary membrane a first composition comprising a test substance; and
 d. examining the pupillary membrane to determine the effect of the test substance on the problematic capillary vessel condition.

Angiogenic Modulators

Any substance, or combination of substances, suspected of having angiogenesis modulation activity can be screened by the method. Such substance can include a purified preparation of compound, an extract from a plant or animal tissue, or a microorganism, and can be prepared in a suitable form for use in the method of the invention by persons skilled in the art. The angiogenic modulator can be administered as an emulsion, a suspension, or a true solution of the test substance in a suitable liquid vehicle, including saline. Such substances can also include viral vector constructs, cell lines, monoclonal and polyclonal antibodies, and small molecules. Small molecules can comprise chemical compounds and elements, low molecular weight carbohydrates, and peptides. Small molecules include non-native substances of the human body; Angiopoitin and VEGF are examples of native substances of the human body.

The angiogenic model can include both pro- and anti-angiogenic substances. Pro-angiogenic substances produce effects characterized by the formation of new capillary structure, by proliferation of endothelial cells, by migration of endothelial cells to extend capillaries, and/or by formation of capillary "sprouts". Examples of pro-angiogenic substances include a proteinaceous and non-proteinaceous molecule, including by example angiogenic growth factors bFGF, aFGF and VEGF. The pro-angiogenic substance VEGF can effect proliferation of endothelial cells, but can not alone effect either migration of endothelial cells to extend capillaries or formation of capillary "sprouts". The substances can be used alone, in mixtures, or in combination with other compounds or substances, to test for angiogenesis. For example, the substances VEGF and Angiopoietin-2 can be tested in combination, or serially, in the same assay.

Anti-angiogenic substances are characterized by inhibiting angiogenic activity. Such substances can include a proteinaceous or non-proteinaceous molecule, and can be selected from corticosteroids, anti-growth factor antibodies and anti-angiogenic proteins such as platelet factor 4. Preferred anti-angiogenic substances include one or more of the following: heparin, low molecular weight heparin, suramin, 3-hydrocortisone, polyclonal neutralizing antibodies for acidic fibroblast growth factor (anti-aFGF), polyclonal neutralizing antibodies for basic fibroblast growth factor (anti-bFGF), polyclonal neutralizing antibodies for vascular endothelial growth factor (anti-VEGF), and mixtures thereof.

Small molecule compounds can be studied by the method of the present invention to determine the substance's effect on capillary vessel structure and its properties which can include the elasticity of the capillary vessels.

While the assay is generally used in the evaluation of the effects and potential uses of test substances on blood vessel systems, such as the PM, the procedure can be used to provide an effective treatment for a persistent PM in a vital mammal, including a human. While cases of persistent PM in human infants are rare, they can be troublesome if the membrane does not dissipate after birth. The assay of the present invention provides a method of treating a persistent PM in a human. The method comprises the steps of: providing a mammal with an eye having a persistent pupillary membrane; and injecting transcorneally proximate to the persistent pupillary membrane an effective amount of an anti-angiogenic substance, whereby the persistent pupillary membrane is reduced or eliminated.

The following examples are offered by way of illustration and are not intended to limit the invention in any manner.

EXAMPLES OF THE INVENTION

Example 1

A Sprague-Dawley rat pup, available from Taconic Farms (German Town, N.Y.), aged postconception (p.c.) day 30.5 to p.c. 34.5, was subdued with metaphane and subsequently anaesthetized with an intramuscular injection of ketamine and xylazine at 1.6 mg/g and 32 mg/g respectively. The depth of anesthesia was monitored by paw pinch response and where necessary, the subject pup was maintained under anesthesia with additional doses of ketamine and xylazine intraperitoneally. The right eyelid of the rat pup was parted at the suture using a microdissecting vanna (Storz, St Louis), the eyeball gently raised, and the eyelids folded underneath to permit illumination of the eye with optic fibre light guides. The local anesthetic tetracaine hydrochloride (0.5%) was applied to the eyeball prior to parting of the eyelids. The rat pup was then placed in a silastic body mold designed to reduce movement, and kept warm with an overlaid heating element from a battery powered boot warmer (L. L. Bean, Maine). The liquid phase for the water immersion microscope objective was provided by addition of a bead of phosphate-buffered saline between the eyeball and the objective. Capillaries of the pupillary membrane were readily detected by searching through the focal axis. An eye holder as shown in FIG. 1 held the eyeball to limit movement, and to illuminate the interior of the eye.

A 5× air objective of a Zeiss Axiophot microscope (Zeiss, Thornwood, N.Y.) was positioned above the cornea of an anaesthetized rat. A beveled glass needle mounted on a micromanipulator was axially apposed to the eye holder and in this position could penetrate the cornea for delivery of the test substance directly onto the pupillary membrane.

A defined volume of a test substance was delivered to the anterior chamber using a Nanoject Variable injector (Drummond, Pa.). Injection was observed with the objective into the right anterior chamber of the eye.

After the predetermined period of angiogenic progress, the rat pup was humanely sacrificed. The treated PM was prepared as a whole mount specimen by dissecting the retina, sclera, choroid and cornea away from the lens, iris diaphragm, hyaloid vessels and pupillary membrane. The latter tissue group was then fixed overnight in 2% glutaraldehyde in 0.1 M cacodylate pH 7.4, 0.1 M sucrose. After fixation, the tissue was washed in buffer alone and dehydrated in an ethanol series (50%, 70%, 80%, 90%, 95% and 100%). The specimens where then treated for 1 hour in hexamethyldisilazane (Polysciences Inc. Pennsylvania) and then air dried overnight. After drying, they were mounted and sputter coated with approximately 100 angstroms of gold-palladium. Specimens were visualized using a JOEL SEM 840 scanning electron microscope.

The angiogenic effect on the cellular/vascular PM system was observed and recorded with imaging and recording means. Image recording was provided by a combination of a CCD camera (DXC-760, Sony) and Betacam SP UVW-1400 video recorder (Sony). A Betacam SP PVW-2650 video deck (Sony) was used for its frame search feature and digital images obtained from videotape using a Matrox frame grabber board that was a component of an imaging system combining Metamorph software and a DECpc XL560 computer (Universal Imaging, New York). The presented vital images were generated by combining overlapping, in focus video frames captured as still images. Figures were assembled using Adobe Photoshop and Quark Express software.

Example 2

Using the method of Example 1, the effects on the PM vascular system by the compounds VEGF and Angiopoitin-2 (Ang2) were examined. Ang2 (biotinylated recombinant human Ang2, available from Calbiochem, San Diego, Calif.) was injected (10 nanograms/ml anterior chamber) into the anterior chamber of a first set of rat pups at 5 days after birth (A5). In a second set of pups of the same age, VEGF (recombinant mouse VEGF, the 164 amino acid isoform) was injected (1 nanogram/ml anterior chamber). After 24 hours, the subjects were sacrificed and the PMs fixed and dissected.

Injection of VEGF-A resulted in a significant increase in the number of mitotic cells in the PM blood vessels, compared to the control (the un-injected eye), but did not result in any sprouting of new blood vessels, or in an enlarging of the diameter of existing capillaries.

The injection of Ang2 also resulted in significant increase in the number of mitotic cells in the PM blood vessels, as well as a dramatic increase in the diameter of capillary vessels, shown by a 2.1-fold increase in the width of flattened vessels present in the whole mount preparations, compared to the control.

The injection of Ang2 also resulted in significant staining by HU177 antibody, indicating dramatic collagen remodeling of the basal lamina of the PM of the first set of subjects. The control showed no staining with HU177.

Example 3

Using the method of Example 1, the effects on the PM vascular system by the co-administration of compounds anti-Tie2 blocking antibody and Ang2 were examined. Anti-Tie2 antibody blocks the Tie2 receptors used by VEGF. Recombinant human Ang2 (from Example 2, 10 nanograms/ml) and anti-Tie2 (available from R&D systems, Minneapolis, Minn., 50 nanograms/ml) were injected into the anterior chamber of a third set of rat pups at 5 days after birth (A5). Anti-Tie2 only (50 nanograms/ml) was injected into the anterior chamber of a fourth set of rat pups. After 24 hours, the subjects were sacrificed and the PMs fixed and dissected.

Injections of anti-Tie2 with Ang2 eliminated any increase in the diameter of capillary vessels attributed to Ang2 alone (pup test 1 of Example 2). Injection of anti-Tie2 alone had no effect on capillary vessel diameter, compared to the control.

We claim:

1. A method for evaluating in vivo whether a test substance induces or promotes growth of new vascular tissue, comprising the steps of:
    a. providing a rodent pup having a pupillary membrane system in a first eye;
    b. injecting transcorneally a test substance proximate to the pupillary membrane; and
    c. examining the pupillary membrane to determine whether new vascular tissue has grown.

2. The method according to claim 1 further comprising a step of comparing the new examined tissue growth with that of a control.

3. The method according to claim 2 wherein the control is the pupillary membrane of the other eye.

4. The method according to claim 1 wherein the pupillary membrane is harvested and removed from the remainder of the eye prior to the examining step.

5. The method according to claim 4 wherein the examining step is carried out by computer analysis of at least one image of the pupillary membrane system.

6. The method according to claim 1 wherein the examining step is carried out by computer analysis of at least one image of the pupillary membrane system.

7. A method for evaluating in vivo whether a test substance inhibits or prevents the growth of new vascular tissue, comprising the steps of:
    a. providing a rodent pup having a pupillary membrane system in a first eye;
    b. injecting transcorneally proximate to the pupillary membrane a first composition comprising a first substance that induces new vascular tissue growth;
    c. injecting transcorneally proximate to the pupillary membrane a second composition comprising a test substance; and
    d. examining the pupillary membrane to determine whether new vascular tissue has grown.

8. The method according to claim 7 wherein the first composition and the second composition are injected simultaneously.

9. The method according to claim 7 further comprising a step of comparing the new examined tissue growth with that of a control.

10. The method according to claim 9 wherein the control is the pupillary membrane of the other eye into which only the first composition is injected.

11. The method according to claim 7 wherein the pupillary membrane is harvested and removed from the remainder of the eye prior to the examining step.

12. The method according to claim 11 wherein the examining step is carried out by computer analysis of at least one image of the pupillary membrane system.

13. The method according to claim 7 wherein the test substance is an angiogenic regressor test substance.

14. A method for evaluating in vivo the effect of a small molecule test substance on a property of a capillary vessel structure, comprising the steps of:
  a. providing a rodent pup having a pupillary membrane system in a first eye;
  b. injecting transcorneally proximate to the pupillary membrane a first composition comprising a small molecule test substance; and
  c. examining the pupillary membrane to determine the effect of the small molecule test substance on the property of the capillary vessel structure of the pupillary membrane.

15. The method according to claim 14 wherein the small molecule test substance is selected from the group consisting of a chemical element, a chemical compound, a low molecular weight carbohydrate, a peptide, and mixtures thereof.

16. The method according to claim 14 wherein the property is the elasticity of the capillary vessels.

17. The method according to claim 14 wherein the property is vascular permeability.

18. The method of claim 14 wherein the property of the capillary vessel structure is a problematic vascular condition.

* * * * *

UNITED STATES PATENT AND TRADEMARK OFFICE
CERTIFICATE OF CORRECTION

PATENT NO. : 7,488,573 B2 Page 1 of 1
APPLICATION NO. : 10/519527
DATED : February 10, 2009
INVENTOR(S) : Richard A. Lang et al.

It is certified that error appears in the above-identified patent and that said Letters Patent is hereby corrected as shown below:

Column 1, line 10,
insert the following

--GOVERNMENT RIGHTS
This invention was made with Government support by the U.S. National Institute of Health, grant RO1 EY10559. The government has certain rights in this invention.--

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,488,573 B2  
APPLICATION NO. : 10/519527  
DATED : February 10, 2009  
INVENTOR(S) : Richard A. Lang et al.

It is certified that error appears in the above-identified patent and that said Letters Patent is hereby corrected as shown below:

Column 1, line 10,  
insert the following

--GOVERNMENT RIGHTS  
This invention was made with Government support under grant number R01 EY010559 awarded by the National Eye Institute. The government has certain rights in this invention.--

This certificate supersedes the Certificate of Correction issued March 23, 2010.

Signed and Sealed this  
First Day of February, 2011

David J. Kappos  
*Director of the United States Patent and Trademark Office*